United States Patent
Robida et al.

(10) Patent No.: US 8,709,093 B2
(45) Date of Patent: Apr. 29, 2014

(54) TRACHEAL STENT WITH LONGITUDINAL RIBS TO MINIMIZE STENT MOVEMENT, COUGHING AND HALITOSIS

(75) Inventors: Todd Robida, Sherborn, MA (US); Mark Boden, Harrisville, RI (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 154 days.

(21) Appl. No.: 13/191,827

(22) Filed: Jul. 27, 2011

(65) Prior Publication Data

US 2012/0035715 A1    Feb. 9, 2012

Related U.S. Application Data

(60) Provisional application No. 61/371,910, filed on Aug. 9, 2010.

(51) Int. Cl.
*A61F 2/04* (2013.01)
*A61F 2/06* (2013.01)
*A61F 2/20* (2006.01)

(52) U.S. Cl.
USPC ... 623/23.7; 623/1.36; 623/23.64; 623/23.65; 623/9

(58) Field of Classification Search
USPC ............... 623/1.15, 1.36, 1.28–1.29, 1.39
See application file for complete search history.

(56) References Cited

U.S. PATENT DOCUMENTS

| | | | | |
|---|---|---|---|---|
| 5,236,446 | A * | 8/1993 | Dumon | 623/6.16 |
| 6,214,037 | B1 * | 4/2001 | Mitchell et al. | 623/1.11 |
| 6,946,680 | B2 * | 9/2005 | Jang | 257/59 |
| 2003/0065377 | A1 * | 4/2003 | Davila et al. | 623/1.13 |
| 2006/0069425 | A1 * | 3/2006 | Hillis et al. | 623/1.16 |
| 2007/0276486 | A1 | 11/2007 | Marten et al. | |
| 2009/0062927 | A1 * | 3/2009 | Marten et al. | 623/23.65 |
| 2009/0093668 | A1 * | 4/2009 | Marten et al. | 600/7 |
| 2009/0192593 | A1 * | 7/2009 | Meyer et al. | 623/1.42 |
| 2009/0312834 | A1 * | 12/2009 | Wood et al. | 623/1.44 |
| 2010/0100170 | A1 * | 4/2010 | Tan et al. | 623/1.18 |

* cited by examiner

*Primary Examiner* — David H Willse
*Assistant Examiner* — Tiffany Shipmon
(74) *Attorney, Agent, or Firm* — Vidas, Arrett & Steinkraus

(57) ABSTRACT

A tracheal stent is an expandable tubular member having a proximal end, a distal end, an inner surface, and an outer surface. Circumferentially adjacent surface protrusions extend outwardly from the outer surface of the expandable tubular member. These surface protrusions have an outer surface, a first lateral surface and a second lateral surface. When the tracheal stent is deployed, the outer surface of the surface protrusion applies a radial force to a wall of the trachea to remove an airway constriction.

20 Claims, 14 Drawing Sheets

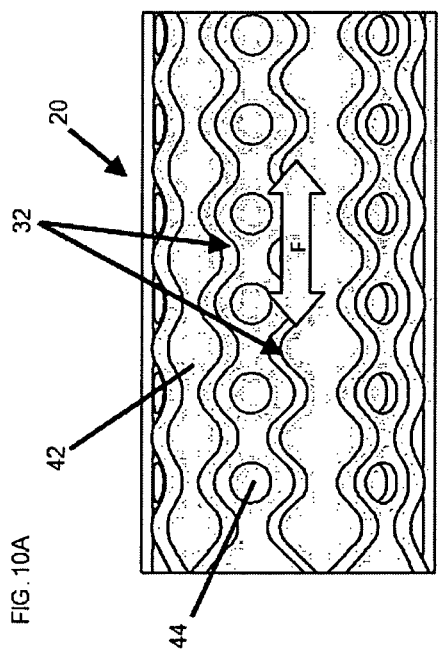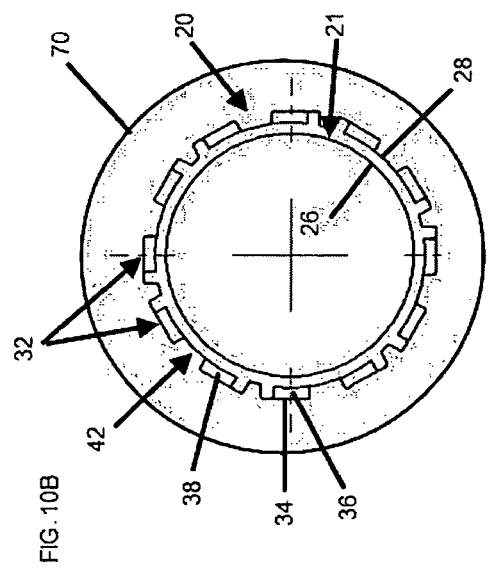

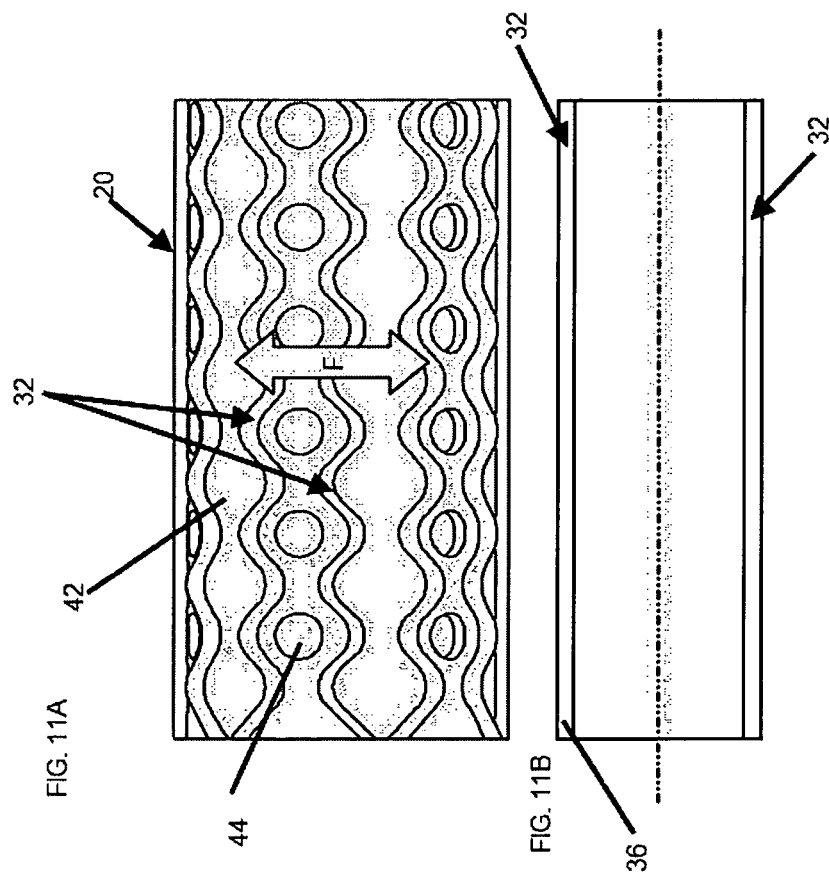

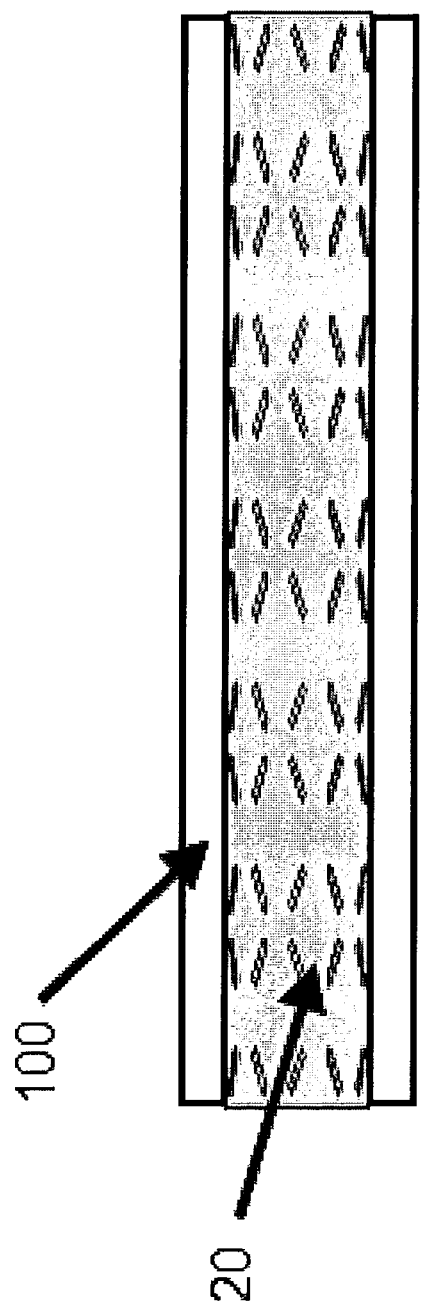

TRACHEAL STENT WITH LONGITUDINAL RIBS TO MINIMIZE STENT MOVEMENT, COUGHING AND HALITOSIS

CROSS REFERENCE TO RELATED APPLICATIONS

This application claims the benefit of U.S. Provisional Application No. 61/371,910, filed on Aug. 9, 2010, the contents of which is hereby incorporated by reference.

BACKGROUND OF THE INVENTION

A stent is a medical device introduced into a body lumen and is well known in the art. A stent is typically delivered in an unexpanded state to a desired location in a bodily lumen and then expanded by an internal radial force. Stents, grafts, stent-grafts, vena cava filters, expandable frameworks, and similar implantable medical devices, collectively referred to hereinafter as stents, are radially expandable endoprostheses, which are typically intravascular implants capable of being implanted transluminally.

Stents have previously been introduced into the trachea when the airway is constricted due to tumor compression, stenosis, and the like. A self-expanding stent can apply pressure outward from the lumen of the stent to the trachea wall to remove the airway constriction. However, these stents may be impermeable or may entirely cover the inside of the trachea, including the cilia that move mucous and inhaled particles upward toward the epiglottis, where the mucous or particles are either swallowed or coughed up. When covered, the cilia are unable to help remove the mucous and other particles from the respiratory system, which can result in the build up of phlegm, halitosis, and excessive coughing in the respiratory tract. Such coughing may also cause displacement of the stent within the trachea.

BRIEF SUMMARY OF THE INVENTION

The present invention is a stent for deployment in a vessel such as the trachea, the stent comprising an expandable tubular member having a proximal end, a distal end, a longitudinal axis extending through the proximal and distal ends, an inner surface, an outer surface, and a uniform thickness between the inner surface and the outer surface. A plurality of surface protrusions extend outwardly from the outer surface of the expandable tubular member. Each surface protrusion has an outer surface, a first lateral surface and a second lateral surface. Each surface protrusion is spaced apart from a circumferentially adjacent surface protrusion. In at least one embodiment, the first lateral surface of the surface protrusion opposes the second lateral surface of the circumferentially adjacent surface protrusion. In at least one embodiment, each surface protrusion is symmetrical to each circumferentially adjacent surface protrusion about the longitudinal axis of the tubular member. The surface protrusions can be ribs (that extend longitudinally along the tubular member from the proximal end of the tubular member to the distal end of the tubular member) or cleats (that are spaced apart both axially and circumferentially from an adjacent cleat). When the stent is deployed in a trachea, the outer surfaces of the surface protrusions apply a radial force to a wall of the trachea to remove an airway constriction.

In some embodiments, a tracheal stent has an expandable tubular member having a proximal end, a distal end, a longitudinal axis extending through the proximal and distal ends, an inner surface, and an outer surface. The tracheal stent also has a plurality of cleats on the outer surface of the tubular member. The cleats extend outwardly from the outer surface of the expandable tubular member, and each cleat has an outer surface, a first lateral surface and a second lateral surface. Each cleat is positioned at an angle relative to the longitudinal axis of the tubular member, and each cleat is spaced apart from a circumferentially adjacent cleat and an axially adjacent cleat. Each cleat is symmetrical to each circumferentially adjacent cleat about the longitudinal axis of the tubular member and each cleat is symmetrical to each axially adjacent cleat about a circumference of the tubular member.

In at least one embodiment, a cleat set is formed with four cleats. The first cleat is circumferentially adjacent to the second cleat, and the third cleat is circumferentially adjacent to the fourth cleat. The first cleat is axially spaced apart from the third cleat, and the second cleat is axially spaced apart from the fourth cleat. The first cleat is symmetrical to the second cleat and the third cleat; the second cleat is symmetrical to the first cleat and the fourth cleat; the third cleat is symmetrical to the first cleat and the fourth cleat; and the fourth cleat is symmetrical to the third cleat and the second cleat. The first cleat is parallel to the fourth cleat and the second cleat is parallel to the third cleat. The cleat set provides the counteracting forces required to hold the stent in position in the trachea.

In at least one embodiment, the tracheal stent further comprises a plurality flow passages formed between adjacent cleats. The flow passages are defined at least by the outer surface of the tubular member, the first lateral surface of each first cleat and the second lateral surface of each adjacent cleat.

In at least one embodiment, the tracheal stent further comprises a plurality of holes positioned in at least one flow passage and extending through the outer surface of the tubular member. In some embodiments, the hole is centered between two cleats. In some embodiments, the hole is centered between the four cleats of the cleat set.

In at least one embodiment the expandable tubular member has a diameter between about 5 mm (0.20 in.) and about 30 mm (1.2 in.).

In some embodiments, the tracheal stent comprises an expandable tubular member having a proximal end, a distal end, a longitudinal axis extending through the proximal and distal ends, an inner surface, and an outer surface; and ribs extending outwardly from the outer surface of the expandable tubular member and longitudinally along the tubular member from the proximal end to the distal end. Each rib has at least an outer surface, a first lateral surface and a second lateral surface. Each rib is spaced apart from a circumferentially adjacent rib. The first lateral surface of the rib opposes the second lateral surface of the circumferentially adjacent rib. In some embodiments, each rib is symmetrical to each circumferentially adjacent surface protrusion about the longitudinal axis of the tubular member.

In at least one embodiment, the ribs have a wave-like pattern with peaks and troughs. The peak of a first rib confronts the trough of a circumferentially adjacent rib such that the first rib is symmetrical to the circumferentially adjacent rib about the longitudinal axis of the tubular member.

In at least one embodiment, circumferentially adjacent ribs form flow passages defined at least by the outer surface of the tubular member, the first lateral surface of each rib and the second lateral surface of each circumferentially adjacent rib.

In at least one embodiment, the tracheal stent further comprises a plurality of holes positioned in at least one flow passage and extending through the outer surface of the tubular member.

In at least one embodiment, a stent anchoring system for deployment in a lumen of a vessel is provided. The stent anchoring system comprises an expandable tubular member having a proximal end, a distal end, a longitudinal axis extending through the proximal and distal ends, an inner surface, an outer surface, a thickness between the inner surface and the outer surface, and a circumference in a plane perpendicular to the longitudinal axis. A plurality of surface protrusions extend outwardly from the outer surface of the expandable tubular member. The surface protrusions each have at least an outer surface, a first lateral surface and a second lateral surface. Each surface protrusion is spaced apart from a circumferentially adjacent surface protrusion. The first lateral surface of the surface protrusion opposes the second lateral surface of the circumferentially adjacent surface protrusion. In at least one embodiment, upon deployment in the vessel lumen having a vessel wall, only the outer surface of each surface protrusion contacts the vessel wall. In some embodiments, each surface protrusion is symmetrical to each circumferentially adjacent surface protrusion about the longitudinal axis of the tubular member.

In at least one embodiment, the surface protrusions are ribs that each extend longitudinally along the tubular member from the proximal end of the tubular member to the distal end of the tubular member. In at least one embodiment, the ribs have a wave-like pattern with peaks and troughs, and the peak of a first rib confronts the trough of a circumferentially adjacent rib such that the first rib is symmetrical to the circumferentially adjacent rib about the longitudinal axis of the tubular member.

In at least one embodiment, the surface protrusions are cleats, wherein each cleat is spaced apart both axially and circumferentially from an adjacent cleat. In at least one embodiment, a first cleat, a second cleat, a third cleat and a fourth cleat form a cleat set. In at least one embodiment, the first cleat is circumferentially adjacent to the second cleat, and the third cleat is circumferentially adjacent to the fourth cleat; and the first cleat is axially spaced apart from the third cleat, and the second cleat is axially spaced apart from the fourth cleat.

In at least one embodiment, the stent anchoring system further comprises a plurality flow passages formed between adjacent surface protrusions. The flow passages are defined at least by the outer surface of the tubular member, the first lateral surface of each first surface protrusion and the second lateral surface of each adjacent surface protrusion. When deployed in the lumen of the vessel, the flow passages are further defined by the vessel wall. In at least one embodiment, the stent anchoring system comprises a plurality of holes positioned in at least one flow passage and extending through the outer surface of the tubular member.

In at least one embodiment, the outer surface of the surface protrusion applies a radial force to the vessel wall when the stent is deployed in the lumen of the vessel.

In at least one embodiment, the expandable tubular member has a diameter between about 5 mm (0.20 in.) and about 30 mm (1.2 in.).

In at least one embodiment, the surface protrusions comprise a metal core covered in polymer. In at least one embodiment, the surface protrusions comprise a stiff polymer fiber.

BRIEF DESCRIPTION OF THE SEVERAL VIEWS OF THE DRAWING(S)

FIGS. 10A-10B show a plan view and a cross-sectional view of an embodiment of the stent.

FIGS. 11A-11B show a plan view and a cross-sectional view of an embodiment of the stent shown in FIG. 10A-10B

FIG. 14 shows a stent of the present invention held within a retractable sheath for deployment in the trachea.

DETAILED DESCRIPTION OF THE INVENTION

Figure 1:
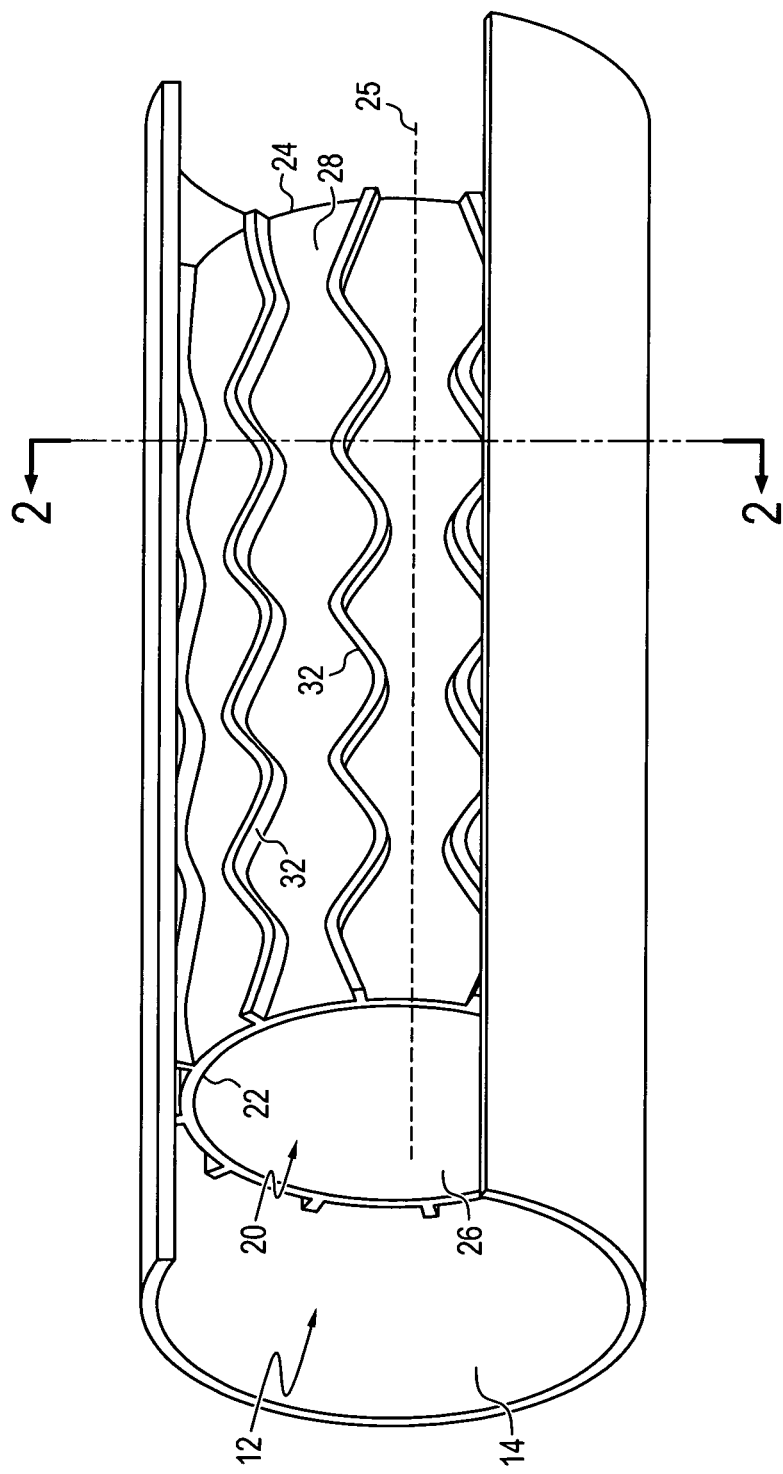
FIG. 1 shows a perspective view of an embodiment of the stent of the present invention, as deployed in the trachea.

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

An embodiment of a stent of the present invention deployed in a trachea is shown in FIG. 1. The trachea 12 has an inner surface 14. The inner surface 14 forms the lumen of the trachea 12, and a plurality of cilia (not shown) line the inner surface 14. Stent 20 is shown deployed in the lumen of the trachea 12. In at least one embodiment, stent 20 is an expandable tubular member 21 that has a proximal end 22, a distal end 24, a longitudinal axis 25 extending through the proximal end 22 and the distal end 24, an inner surface 26, and an outer surface 28.

In at least one embodiment, a plurality of surface protrusions 32 extend outwardly from the outer surface 28 of the tubular member 21, and the surface protrusions 32 are distributed circumferentially about the outer surface 28. In some embodiments (such as the embodiment shown in FIG. 1), the surface protrusions 32 are "ribs" that extend longitudinally along the entire length of the tubular member 21 from the proximal end 22 to the distal end 24. Each rib 32 forms a wave-like pattern on the outer surface 28 of the tubular member 21. In at least the embodiment shown in FIG. 1, first rib 32 has the same wavelength and amplitude as an adjacent rib 32. It is within the scope of the invention that the surface protrusions 32 can have other configurations, some of which will be discussed further below with respect to FIGS. 9-12. In at least the embodiment shown in FIG. 1, each "rib" 32 forms a continuous wave-like pattern on the outer surface 28 of the tubular member 21. In some embodiments, surface protrusions 32 can form a discontinuous wave-like pattern along the length of the tubular member.

In at least the embodiment shown in FIG. 1, each rib 32 forms a wave-like pattern that is symmetrical about the longitudinal axis 25 to the wave-like pattern of an adjacent rib 32. For purposes of this disclosure, "symmetrical" refers to "reflection symmetry," "line symmetry," or "mirror symmetry" where there is at least one line that splits the image in half so that one surface protrusion 32 is the mirror image of an adjacent surface protrusion 32. In the embodiment shown in FIG. 1, this line is longitudinal axis 25 that splits the image in half so that one rib 32 is the mirror image of an adjacent rib 32.

Figure 2:
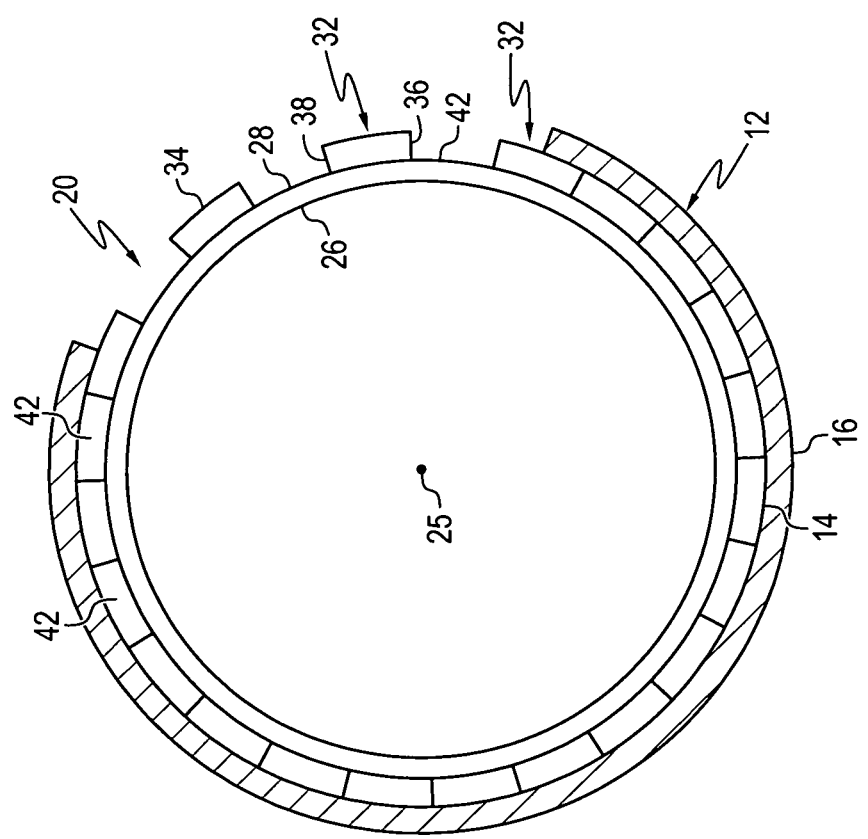
FIG. 2 shows a cross-sectional view of the stent and trachea of FIG. 1.

FIG. 2 shows a cross-sectional view of the stent 20 of FIG. 1 deployed in the trachea 12. As shown in FIG. 2, the tubular member 21 has an inner surface 26 and an outer surface 28. Each rib 32 has an outer surface 34 defined by the length of the rib and the width of the rib, a first lateral surface 36 defined by the length of the rib and the thickness of the rib, and a second lateral surface 38 defined by the length of the rib and the thickness of the rib. In some embodiments, ribs 32 have the same width between the first lateral surface 36 and the second lateral surface 38 along the length of the rib. In some embodiments, the width between the first lateral surface 36 and the second lateral surface 38 can vary along the length of the rib 32, as long as each rib is symmetrical to a circumferentially adjacent rib 32.

As shown in FIG. 2, the outer surface 34 of the ribs 32 contacts the inner surface 14 of the trachea wall. When the stent 20 is deployed in the trachea 12, the ribs 32 apply a radial force over the surface area of the ribs' outer surface 34 to apply pressure outward on the trachea 12 to remove an airway constriction. The ribs 32 also allow the stent 20 to remain in position in the trachea 12 to prevent dislodgement of the stent, as will be discussed further below.

A plurality of flow passages 42 are formed between each rib 32 and an adjacent rib 32. These flow passages 42 are defined at least by the outer surface 28 of the tubular member 21, the first lateral surface 36 of a first rib 32, and the second lateral surface 38 of a second rib 32. The flow passages 42 allow a plurality of cilia (not shown) attached to the inner surface 14 of the trachea 12 to function normally to help remove mucous and other particles from the respiratory system in those areas. Mucous and other particles can thus flow through the flow passages 42 along the stent 20 out to the epiglottis for removal from the respiratory tract. As discussed above, while the rib 32 as shown in FIG. 2 is a continuous member, rib 32 can also be a discontinuous member, which allows for additional flow of mucous between the flow passages 42.

Figure 3:
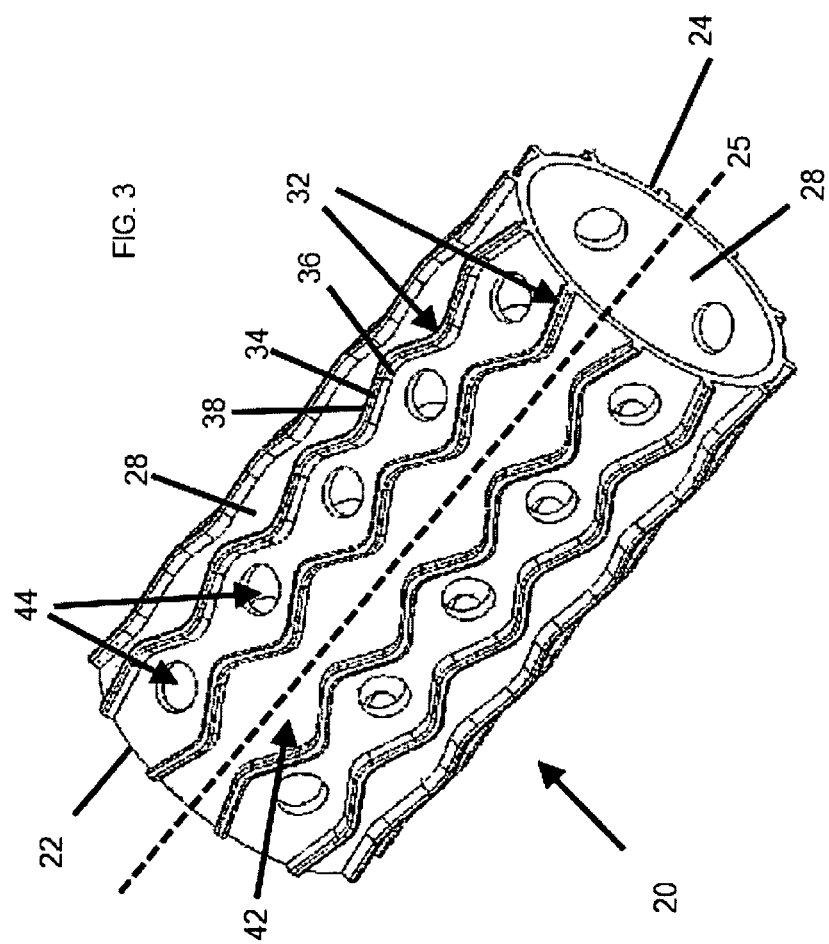
FIG. 3 shows a perspective view of an embodiment of the stent of the present invention.

In some embodiments, such as the embodiment shown in FIG. 3, stent 20 further comprises a plurality of holes 44 that extend through the outer surface 28 of the tubular member 21. In at least one embodiment, holes 44 are positioned in the flow passage 42 between a first rib 32 and an adjacent rib 32 to allow transfer of fluid and help clear waste particles present in the trachea. In at least one embodiment, a first hole 44 is axially aligned with an adjacent hole 44. It is within the scope of the invention that the outer surface has non-circular shaped holes, slots, and/or other structures to help facilitate the transfer of fluid and removal of mucous and other waste particles from the trachea. It is also within the scope of the invention that the outer surface 28 of the tubular member 21 has a varied or non-smooth surface.

In at least one embodiment of the stent 20, the diameter of the stent 20 is between about 5 mm (0.20 in.) and about 30 mm (1.2 in.). In at least one embodiment of the stent, the length of the stent 20 from the proximal end 22 to the distal end 24 is between about 10 mm (0.40 in.) and about 200 mm (7.9 in.). In at least one embodiment, the surface protrusions 32 have a thickness measured from the outer surface 28 of between about 1 mm (0.04 in) and about 10 mm (0.40 in). In some embodiments, this thickness varies along each surface protrusion 32 or varies among each of the surface protrusions 32. In at least one embodiment, a surface protrusion 32 can be spaced apart from an adjacent surface protrusion about 0.2 mm (0.008 in) to about 20 mm (0.79 in). Where the stent 20 has holes 44, in at least one embodiment the holes 44 have a diameter between about 0.2 mm (0.008 in) to about 20 mm (0.79 in).

Figure 4:
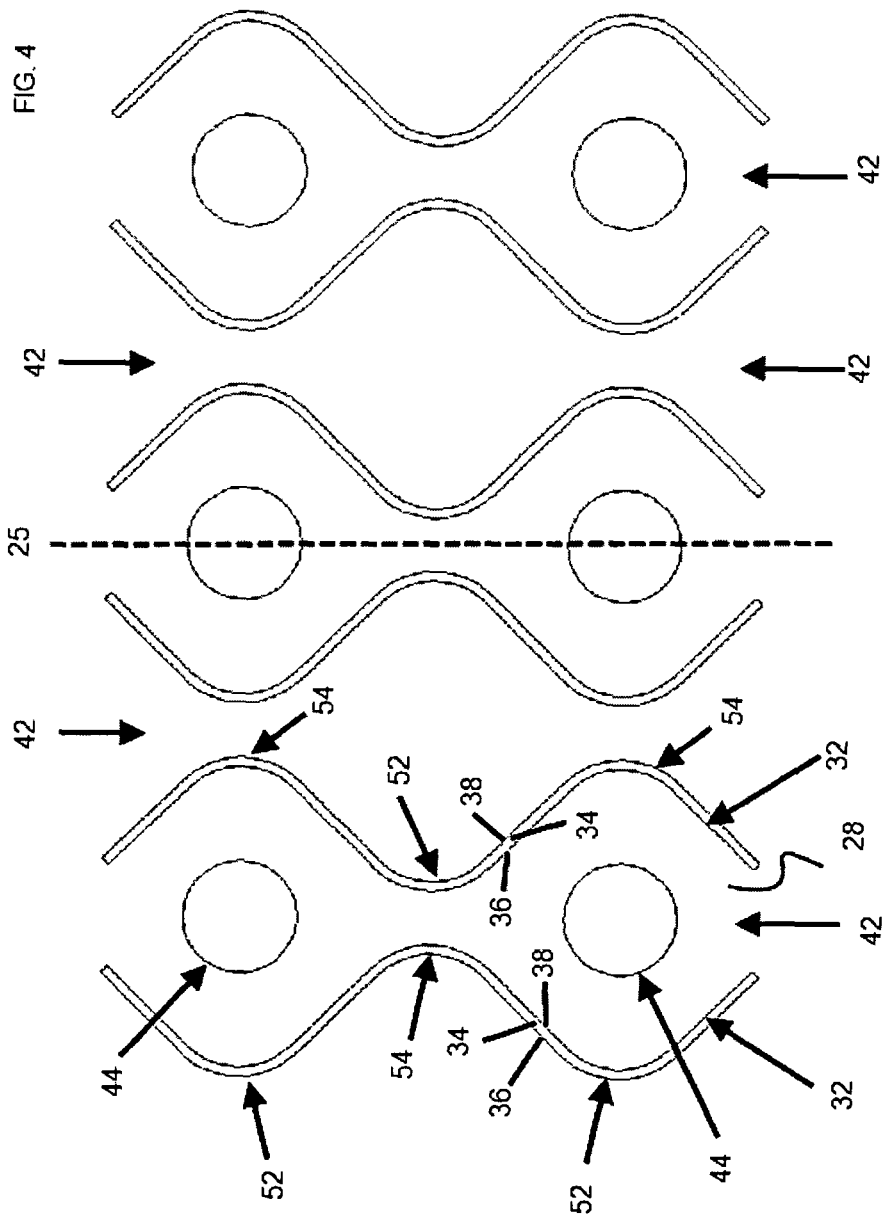
FIG. 4 shows a flat view of a portion of the embodiment of the stent shown in FIG. 3.

FIG. 4 shows a flat view of a portion of the embodiment of the stent 20 shown in FIG. 3. Outer surface 28 has a plurality of ribs 32 and a plurality of flow passages formed between a first rib 32 and an adjacent rib 32. Ribs 32 have an outer surface 34, a first lateral surface 36, and a second lateral surface 38. In at least the embodiment shown in FIG. 4, ribs 32 each have a wave-like pattern with a peak 52 and a trough 54. In at least one embodiment, the wave-like pattern of rib 32 is symmetrical to the wave-like pattern of an adjacent rib 32 about the longitudinal axis 25. In at least one embodiment, rib 32 is symmetrical to an adjacent rib 32 about longitudinal axis 25 such that the peak 52 of the first rib 32 is circumferentially aligned with a trough 54 of an adjacent rib 32, and a trough 54 of the first rib 32 is circumferentially aligned with a peak 52 of a circumferentially adjacent rib 32. In other words, the peak 52 of the first rib 32 confronts a trough 54 of the circumferentially adjacent rib.

In at least one embodiment, at least one hole 44 is positioned in at least one flow passage 42 and extends through the outer surface 28. In some embodiments (such as the embodiment shown in FIG. 4), the hole 44 is positioned in the center of a region of the flow passage 42, the region formed between a peak 52 of a first rib 32 and a trough of an adjacent rib 32. In some embodiments (such as the embodiment shown in FIG. 4), a plurality of holes 44 are axially aligned in the flow passage 42. In some embodiments (such as the embodiment shown in FIG. 4), a plurality of holes 44 can be circumferentially aligned, the holes 44 positioned in different flow passages 42 around the circumference of the stent 20. While FIG. 4 shows a circular hole 44, it is within the scope of the invention that the outer surface 28 has non-circular shaped holes, slots, and/or other structures.

Figure 5:
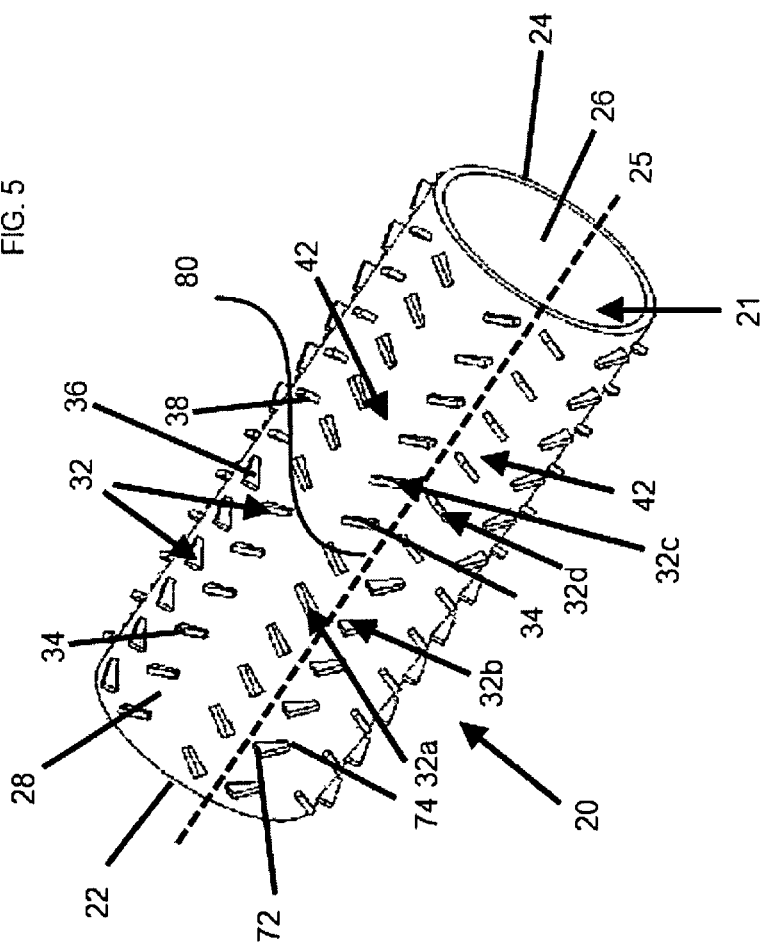
FIG. 5 shows a perspective view of an embodiment of the stent of the present invention.
Figure 6:
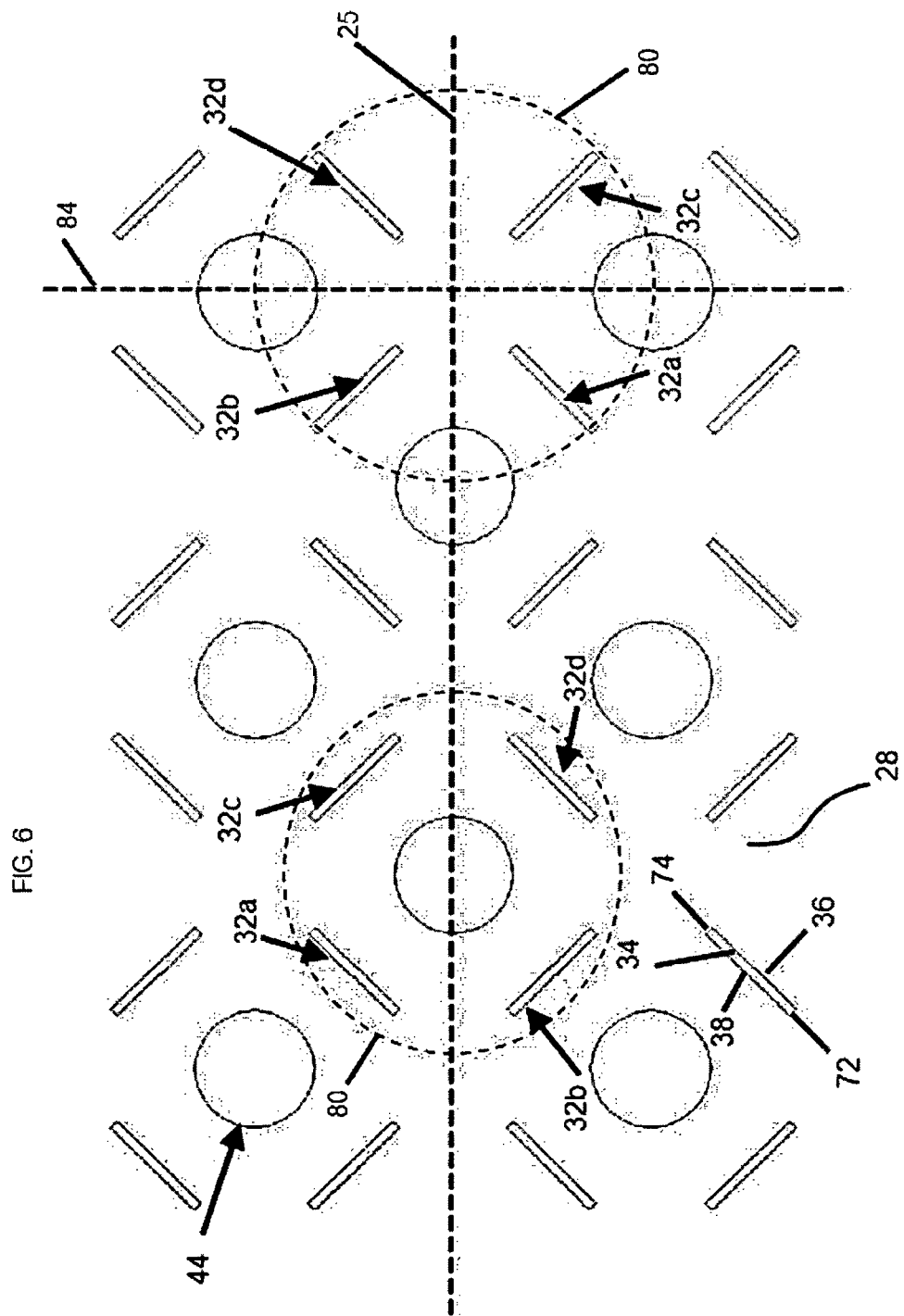
FIG. 6 shows a flat view of a portion of an embodiment of the stent.

Besides surface protrusions 32 that are continuous members from the proximal end to the distal end (as shown with the ribs in FIGS. 1-4), in some embodiments (as shown in FIG. 5) stent 20 has smaller "cleat-like" surface protrusions 32 on the outer surface 28 of the stent 20. In FIG. 5, a plurality of these cleats 32 extend from a proximal end 22 to a distal end 24 and are spaced apart both axially and circumferentially. As shown in FIG. 5, each cleat is symmetrical to each circumferentially adjacent cleat about the longitudinal axis 25 of the tubular member. In some embodiments (such as shown in FIG. 6), each cleat is also symmetrical to each axially adjacent cleat about a circumference of the tubular member. For purposes of this disclosure, "symmetrical" refers to "reflection symmetry," "line symmetry," or "mirror symmetry" where there is at least one line that splits the image in half so that one surface protrusion 32 is the mirror image of an adjacent surface protrusion 32. In the embodiment shown in FIG. 5, this line is longitudinal axis 25 that splits the image in half so that one cleat 32 is the mirror image of an adjacent cleat 32. Because each cleat can also be symmetrical to an axially adjacent cleat, another line of symmetry exists along a circumferential line perpendicular to the longitudinal axis, as shown in FIG. 6.

Each cleat 32 has an outer surface 34, a first lateral surface 36, and a second lateral surface 38, a first end surface 72, and a second end surface 74. The first lateral surface 36 is defined by the length of the cleat and the thickness of the cleat, and the second lateral surface 38 defined by the length of the cleat and the thickness of the cleat. The first end surface 72 is defined by the width of the cleat and the thickness of the cleat, and the second end surface 74 defined by the width of the cleat and the thickness of the cleat. In the embodiment shown, the first lateral surface 36 is parallel to the second lateral surface 38, and the first end surface 72 is parallel to the second end surface 74. In other embodiments, the surfaces 36, 38, 72, 74 may have different geometrical configurations. For example, the surfaces 36, 38, 72, and 74 can be concave or the surfaces can be wave-like. In some embodiments, cleats 32 have the same width between the first lateral surface 36 and the second lateral surface 38 along the length of the cleat. In some embodiments, the width between the first lateral surface 36 and the second lateral surface 38 can vary along the length of the cleat 32, as long as cleat rib is symmetrical to a circumferentially adjacent rib 32.

The outer surface 34 of the cleats 32 contacts the inner surface 14 of the trachea wall. When the stent 20 is deployed in the trachea 12, the cleats 32 apply a radial force over the surface area of the cleats' outer surface 34 to apply pressure outward on the trachea 12 to remove an airway constriction. The cleats 32 also allow the stent 20 to remain in position in the trachea 12.

A plurality of flow passages 42 are formed between each cleat 32 and a circumferentially adjacent cleat 32. Flow passages 42 are also formed between each cleat 32 and an axially adjacent cleat 32. These flow passages 42 are defined at least by the outer surface 28 of the tubular member 21, the first lateral surface 36 of a first rib 32, and the second lateral surface 38 of a second rib 32. The flow passages can be further defined by the first end surface 72 and the second end surface 74 of each cleat 32. The flow passages 42 allow the cilia (not shown) attached to the inner surface 14 of the trachea 12 to function normally to help remove mucous and other particles from the respiratory system in those areas. Mucous and other particles can thus flow through the flow passages 42 along the stent 20 out to the epiglottis for removal from the respiratory tract.

FIG. 6 shows a flat view of the embodiment of the stent 20 with cleats 32 on the outer surface 28 of the stent 20. A plurality of cleats 32a, 32b, 32c, 32d form cleat sets 80. Cleat 32a is circumferentially adjacent to cleat 32b, and cleat 32c is circumferentially adjacent to cleat 32d. In each cleat set 80, cleat 32a and 32b are mirror images of each other along the longitudinal axis 25 of the stent 20, and cleat 32c and 32d are symmetrical to other along the longitudinal axis 25. Cleat 32a is also axially adjacent to cleat 32c, and cleat 32b is axially adjacent to cleat 32d. In each cleat set 80, cleat 32a and 32c are symmetrical to each other, along a circumference 84 of the stent and cleat 32b and 32d are symmetrical to each other along the circumference 84 of the stent. In this way, cleats 32a, 32b, 32c, and 32d provide the counteracting forces required to hold the stent 20 in position in the trachea.

Referring back to FIG. 5, a cleat set 80 is also shown in that figure. In this cleat set, cleat 32a is not axially adjacent to cleat 32c, but rather cleat 32a is axially aligned with cleat 32c. However, cleats 32a and 32c symmetrical to each other along a circumference of the stent, and cleats 32b and 32d are symmetrical to each other along the circumference of the stent. The cleats 32a, 32b, 32c, and 32d in FIG. 5 also provide the counteracting forces required to hold the stent 20 in position in the trachea.

FIG. 6 also shows a plurality of holes 44 in the outer surface 28 of the stent. In some embodiments, at least one hole 44 is positioned in at least one flow passage 42 and extends through the outer surface 28. In some embodiments, the hole 44 is positioned in the center of a cleat set 80. In some embodiments, the holes 44 are axially aligned in the flow passage 42. In some embodiments, the holes 44 can be circumferentially aligned with the holes 44 positioned in different flow passages 42 around the circumference of the stent 20.

Figure 7:
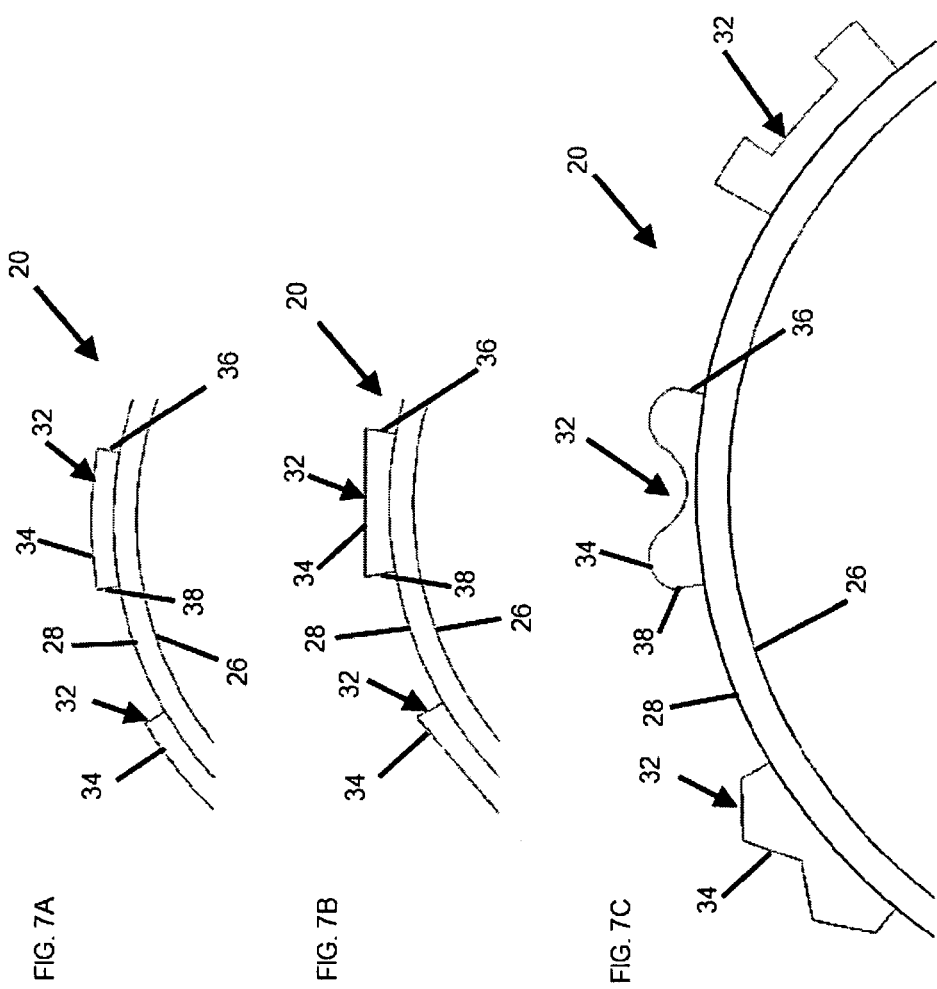
FIGS. 7A-7C show portions of cross-sectional views of embodiments of the stent.

Regardless of whether the surface protrusions 32 are ribs or cleats, in some embodiments, the outer surface 34 of the surface protrusions 32 can have a rounded profile (as shown in FIG. 7A). In some embodiments, the outer surface 34 of the surface protrusions 32 can have a flat profile (as shown in FIG. 7B). Such a flat profile will help to increase friction as the stent 20 contacts the inner surface 14 of the trachea. In other embodiments, the outer surface 34 can have raised features (as shown in FIG. 7C). These various profiles allow the stent 20 to contact the surface of the trachea wall and apply pressure as desired.

Regardless of whether the surface protrusions 32 are ribs or cleats, the intersection of each protrusion 32 with the outer surface 28 of the tubular member can have a radius or fillet to allow mucous to flow easier and to reduce any stress concentrations that may exist between at that intersection. In some embodiments, the surface protrusions 32 can be tapered.

In some embodiments, the ribs or cleats can have flared ends for additional securement of the stent in the trachea. In at least one embodiment, such as the embodiment shown in FIG. 8, stent 20 has a tubular member 21 and a plurality of ribs 32 extending from the outer surface 28 of the tubular member 21. Each rib 32 has an outer surface 34, a first lateral surface 36, and a second lateral surface 38. The ribs 32 are continuous, straight ribs. In the configuration shown, a first rib 32 is parallel to an adjacent rib 32. In at least one embodiment, the ribs 32 can have other configurations, such as wave-like configurations as previously shown. In at least one embodiment, ribs 32 which have a flared end 90 at each end of the rib 32, which helps prevent movement of the stent 20 in the trachea. The thickness of the rib 32 (measured between the outer surface 34 of the rib and the outer surface 28 of the tubular member) is greater at the flared ends 90 than at the non-flared regions of the rib 32. A plurality of flow passages 42 are formed between each rib 32 and an adjacent rib 32 to help facilitate cilia movement.

Figure 8:
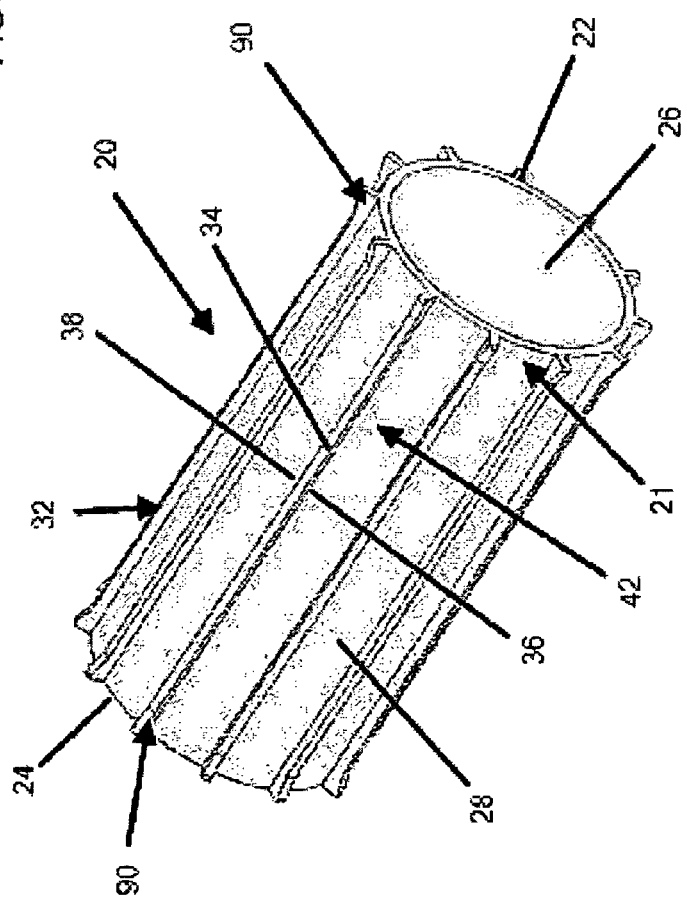
FIG. 8 shows a perspective view of an embodiment of the stent.

As shown in FIG. 8, the ribs 32 are aligned with the longitudinal axis of the stent 20. In some embodiments, the ribs 32 can be helically arranged along the outer surface 28 of the tubular member to provide additional resistance to migration. In some embodiments, the ribs 32 can be formed in a single helix in order to promote mucous movement, particularly where the ribs 32 are continuous members. Where the ribs 32 are discontinuous members, the ribs can be formed in a broken double helix to also promote mucous movement.

Regardless of whether the surface protrusions 32 are ribs or cleats, in some embodiments, the end surfaces 72, 74, 90 of the surface protrusions 32 can be rounded, flat, or have other geometrical configurations.

In at least one embodiment, stent 20 can have surface protrusions 32 that are ribs and surface protrusions 32 that are cleats.

Figure 9:
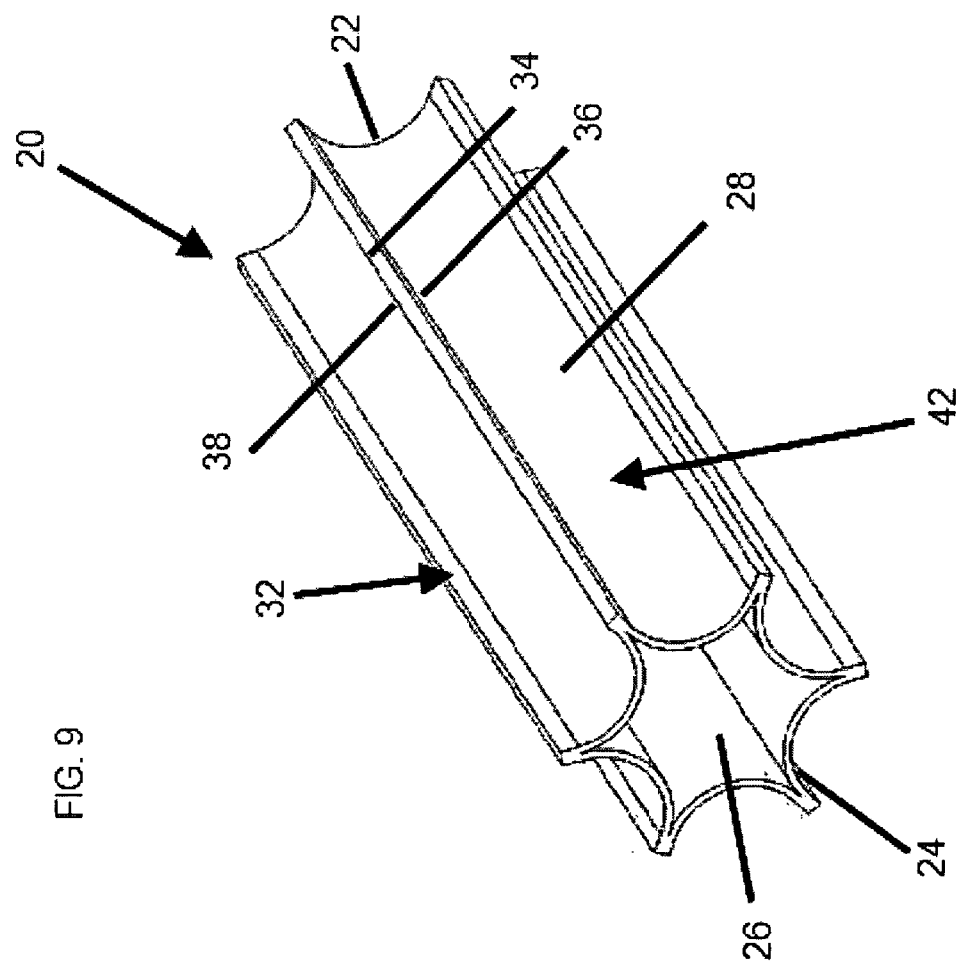
FIG. 9 shows a perspective view of an embodiment of the stent.

While the previous embodiments shown all have circular cross-sections, in at least one embodiment (as shown in FIG. 9), stent 20 has a non-circular cross-section. In this embodiment, ribs 32 extend outwardly from the outer surface 28 of the 20 stent about 5 mm (0.04 in) to about 30 mm (0.40 in). Each rib 32 has an outer surface 34, a first lateral surface 36, and a second lateral surface 38. Each rib 32 as shown is a continuous, straight rib. In some embodiments, each rib has a fillet at the intersection between at least one lateral surface 32, 34 and the outer surface 28 of the stent. In the configuration shown in FIG. 9, a first rib 32 is parallel to an adjacent rib 32. A plurality of flow passages 42 are formed between each rib 32 and an adjacent rib 32 to help facilitate cilia movement. The stent 20 is concave in the flow passages 42 between the ribs 32. When the stent 20 is deployed in the trachea 12, the ribs 32 apply a radial force over the surface area of the ribs' outer surface 34 to apply pressure outward on the trachea 12 to remove an airway constriction. The ribs 32 also allow the stent 20 to remain in position in the trachea 12, as will be discussed further below. In some embodiments, the cross-section of the stent is defined by the number of ribs 32 on the stent. As shown in FIG. 9, six ribs 32 form a hexagonal cross-section. An embodiment of the stent having three ribs 32 would form a triangular cross-section. An embodiment of the stent having four ribs 32 would form a rectangular or square cross-section.

In some embodiments, the stent can comprise spun fibers in a woven, braided, knit, twisted, welded or otherwise connected wire formation. In some embodiments, the stent can comprise a solid tube. In some embodiments, the surface protrusions on the stent can comprise a metal core covered in polymer or a stiff polymer fiber. Suitable materials for the stent include, but are not limited to, biocompatible thermoplastic elastomers (TPE) such as C-Flex, styrenic block co-polymers such as those made by Kraton, styrene isobutylene styrene such as the Nortech brand, silicone polyurethanes, nylons, shape memory materials, and other biodegradable metals, polymers, and composites. In at least one embodiment, the entire stent, including the raised members can be covered in a smooth polymer material.

In some embodiments of the invention, the stent, or portion thereof, may be provided with a substance. The substance can be disposed on any of the surfaces of the stent or within holes in the stent surface using any known technique for doing so. The substance may be a coating or a portion of the stent constructed and arranged to deliver the substance to a location in a body lumen. The substance may be a drug, genetic material, cells, a non-genetic therapeutic agent, a polymer matrix having a therapeutic component or any other substance which it would desirable to deliver into a body lumen. In some embodiments, the stent can be loaded with a substance such as microbicides, silver, quaternary ammonium salts, peptide-based compounds, and other substances that prevent septic issues. In some embodiments the stent can be loaded with drugs that are either anti-inflammatory or anti-tumor. In some embodiments, the stent can be provided with anti-bacterial or anti-fouling substances. In some embodiments, the stent may include a lubricating agent.

Figure 12:
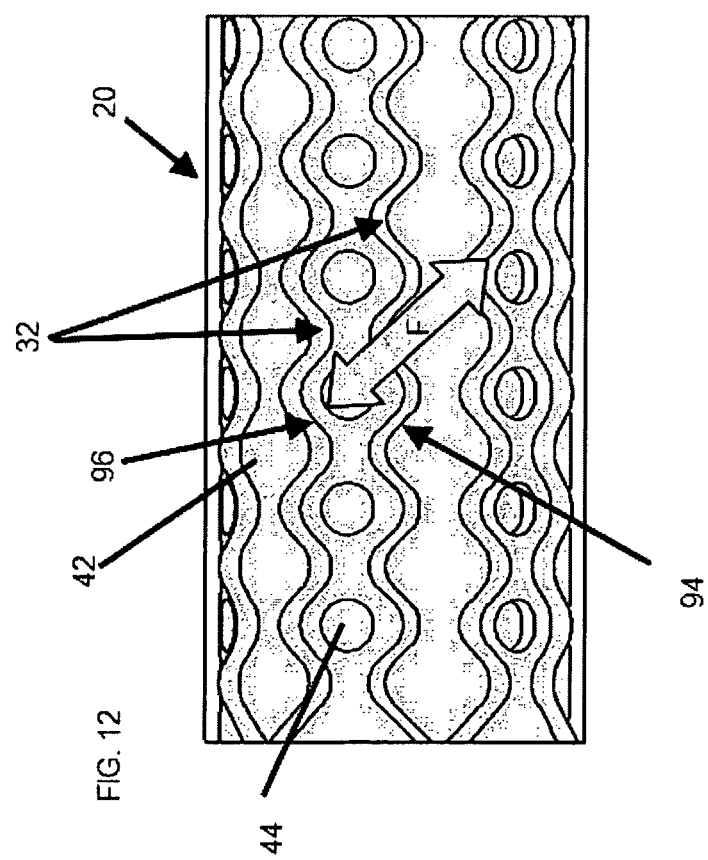
FIG. 12 shows a plan view of an embodiment of the stent shown in FIG. 10A.

When deployed within the lumen of the trachea 12 (as shown in FIGS. 1-2), stent 20 may be exposed to three types of motion: linear motion, rotational motion, or a combination of linear motion and rotational motion. FIGS. 10-12 show the stent 20 in each of these modes of motion and how the stent 20 opposes the applied force F. Force F is any force that could cause movement of the stent including distortions of the trachea due to coughing, bending of the upper torso and/or spine, twisting of the upper torso and/or spine, seizures, and other forces that can cause the stent to dislodge from its position.

FIGS. 10A-10B show the stent 20 (as depicted in FIGS. 3-4) exposed to a force F applied in the axial direction to create linear movement of the stent 20. FIG. 10B is a cross-sectional view of stent 20, the cross-section being perpendicular to the force F. FIG. 10B shows the effective profile 92 of stent 20 that opposes force F, wherein the effective profile 92 is perpendicular to the force F. In this profile, ribs 32 cover a greater portion of the effective profile 92 than the remainder of the effective profile (in other words, the flow passages 42). As long as the ribs 32 cover a greater portion of the effective profile 92 in opposing force F, the stent 20 will remain in place.

FIGS. 11A-11B show the stent 20 (as depicted in FIGS. 3-4) exposed to a force F in the tangential direction to create rotational movement of the stent 20, and the effective profile 92 of stent 20 that opposes force F. Here again, ribs 32 cover a greater portion of the effective profile 92 than the remainder of the effective profile 92. However, in this case, the ribs 32 cover the entire portion of the effective profile 92 to prevent movement of the stent 12.

FIG. 12 shows the stent 20 exposed to a force F in both the axial direction and the tangential direction to create both linear and rotational movement of the stent 20. Here, a portion 94 of the geometry of ribs 32 are parallel to the applied force F, while a portion 96 of the geometry of the ribs are perpendicular to the applied force F along the effective profile (not shown). As long as the opposing portion 96 is greater than the facilitating portion 94, movement of stent 20 will be prevented. Because the ribs 32 are symmetrical to one another, the force will act on a given portion of the rib as much as it is resisted by a symmetrical portion of the rib. Thus, movement of the stent 20 will be prevented.

Figure 13:
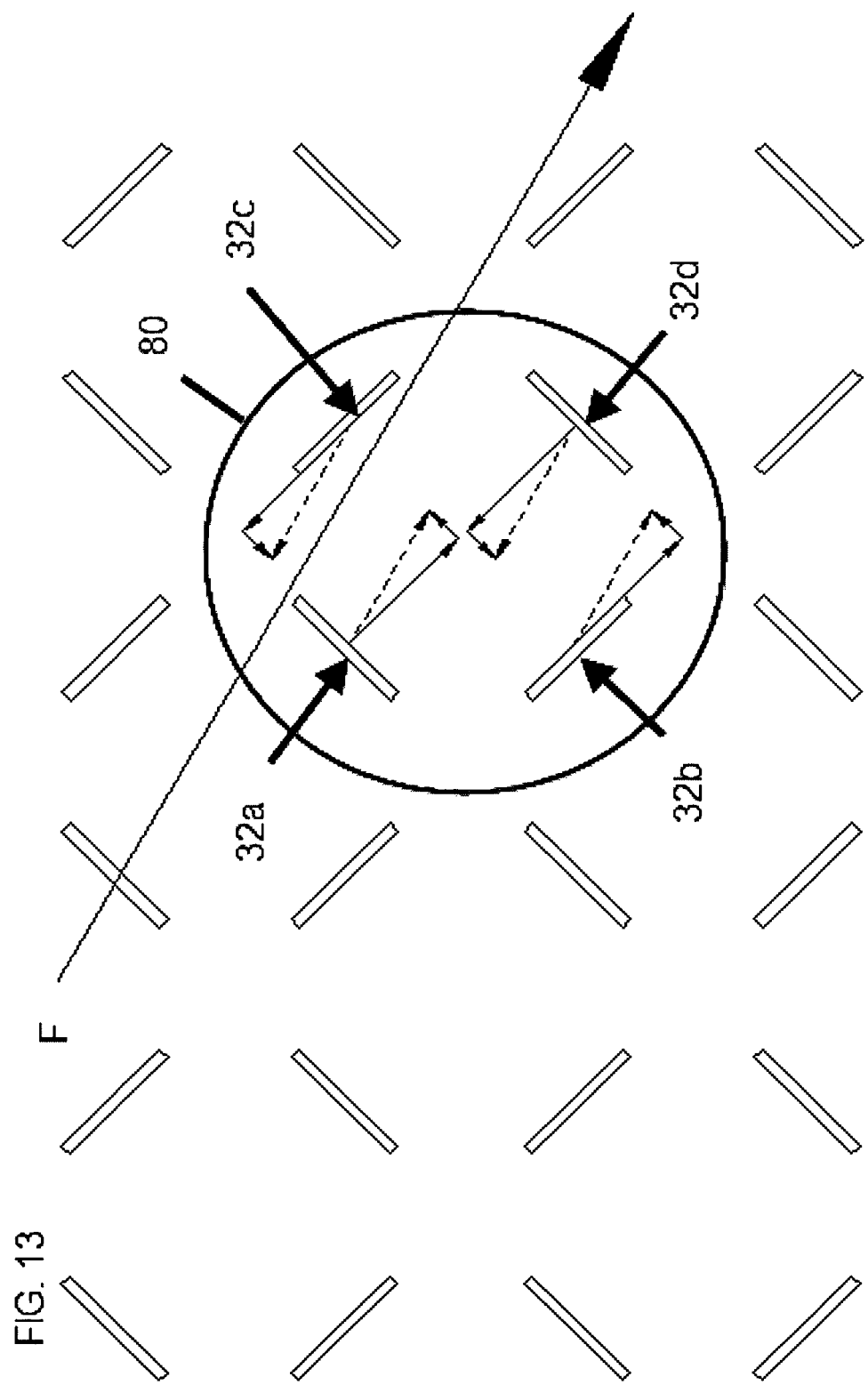
FIG. 13 show a plan view of an embodiment of the stent shown in FIG. 5.

These same principles apply to the stent 20 where the surface protrusions 32 are cleats. As shown in FIG. 13, a force F acts on a cleat set 80, particularly cleats 32a and 32b. Force F is resisted by cleats 32c and 32d. Because the cleats 32a, 32b, 32c and 32d are symmetrical to one another, the force acts on cleats 32a and 32b as much as it is resisted by cleats 32c and 32d. Thus, movement of the stent 20 will again be prevented.

In some embodiments as shown in FIG. 14, the stent 20 can be provided with a retractable sheath 100 that holds the device in a compressed state until it can be deployed as a self-expandable stent. During deployment, as the sheath is retracted and the exposed portion of the stent expands, the radial force of the expansion of the stent pushes the outer surface 34 of the surface protrusions 32 against the trachea wall to remove an airway constriction from the trachea. The flow passages 42 allow for the cilia that line the trachea wall to move particles and mucous from the trachea.

In at least one embodiment of the invention, a stent-graft assembly may be provided. Surface protrusions are located on an outer surface of an external graft with a self-expanding stent disposed within an inner surface of the graft. The stent-graft assembly may be a single unit. In some embodiments, the stent and graft are delivered simultaneously. In some embodiments, the stent and graft are delivered separately.

The above disclosure describes using the stent in the trachea. However, the invention may be used in any application involving expansion of a vessel (or support of a vessel wall) where a flow path on an outer surface of the stent is required, such as in the bilary duct and the duodenum.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to." Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below (e.g. claim 3 may be taken as alternatively dependent from claim 2; claim 4 may be taken as alternatively dependent on claim 2, or on claim 3; claim 6 may be taken as alternatively dependent from claim 5; etc.).

This completes the description of the preferred and alternate embodiments of the invention. Those skilled in the art may recognize other equivalents to the specific embodiment described herein which equivalents are intended to be encompassed by the claims attached hereto.

The invention claimed is:

1. A stent anchoring system for deployment in a lumen of a vessel, the system comprising:
   an expandable tubular member having a proximal end, a distal end, a longitudinal axis extending through the proximal and distal ends, an inner surface, an outer surface, a thickness between the inner surface and the outer surface, and a circumference in a plane perpendicular to the longitudinal axis; and
   a plurality of cleats extending outwardly from the outer surface of the expandable tubular member, each cleat having an outer surface, a first lateral surface, a second lateral surface, and end surfaces, wherein the first and second lateral surfaces are longer than the end surfaces, the plurality of cleats defining flow passages therebetween, wherein each cleat is positioned at a non-parallel angle to the longitudinal axis of the expandable tubular member, and each cleat is spaced apart both axially and circumferentially from an adjacent cleat and further wherein each cleat is symmetrical to each circumferentially adjacent cleat about the longitudinal axis of the tubular member.

2. A stent anchoring system for deployment in a lumen of a vessel, the system comprising:
   an expandable tubular member having a proximal end, a distal end, a longitudinal axis extending through the proximal and distal ends, an inner surface, an outer surface, a thickness between the inner surface and the outer surface, and a circumference in a plane perpendicular to the longitudinal axis; and
   a plurality of cleats extending outwardly from the outer surface of the expandable tubular member, each cleat having an outer surface, a first lateral surface, a second lateral surface, and end surfaces, wherein the first and second lateral surfaces are longer than end surfaces of the cleat, each cleat spaced apart from a circumferentially adjacent surface protrusion, the plurality of cleats defining flow passages therebetween, wherein each cleat is positioned at a non-parallel angle to the longitudinal axis of the expandable tubular member, and each cleat is spaced apart both axially and circumferentially from an adjacent cleat, the plurality of cleats forming a plurality of cleat sets wherein the lateral sides of cleats in a cleat set define a cleat area; and
   a plurality of holes extending through the outer surface of the tubular member and sized to allow transfer of fluid therethrough, wherein each hole is positioned in a cleat area.

3. The stent of claim 1, further wherein each cleat is symmetrical to each axially adjacent cleat about a circumference of the tubular member.

4. The stent anchoring system of claim 1, further wherein a first cleat, a second cleat, a third cleat and a fourth cleat form a cleat set wherein:
   the first cleat is circumferentially adjacent to the second cleat, and the third cleat is circumferentially adjacent to the fourth cleat; and
   the first cleat is axially spaced apart from the third cleat, and the second cleat is axially spaced apart from the fourth cleat.

5. The stent of claim 4, wherein the first cleat is symmetrical to the second cleat and the third cleat; the second cleat is symmetrical to the first cleat and the fourth cleat; the third cleat is symmetrical to the first cleat and the fourth cleat; the fourth cleat is symmetrical to the third cleat and the second cleat; and the first cleat is parallel to the fourth cleat and the second cleat is parallel to the third cleat.

6. The stent of claim 4, wherein the first cleat is perpendicular to the second cleat and the third cleat; the second cleat is perpendicular to the first cleat and the fourth cleat; the third cleat is perpendicular to the first cleat and the fourth cleat.

7. The stent anchoring system of claim 1, wherein, the outer surface of the cleat applies a radial force to the vessel wall.

8. The stent anchoring system of claim 1, wherein the expandable tubular member has a diameter between about 5 mm and about 30 mm.

9. The stent anchoring system of claim 1, wherein the cleats comprise a metal core covered in polymer.

10. The stent anchoring system of claim 1, wherein the cleats comprise a stiff polymer fiber.

11. The stent anchoring system of claim 1, wherein the plurality of cleats have a geometry that counteracts linear motion, rotational motion, and a combination of linear motion and rotational motion of the expandable tubular member due to a force applied to the tubular member.

12. The stent anchoring system of claim 1, wherein the plurality of cleats are arranged such that a greater portion of a cross-sectional profile of the tubular member is covered by the plurality of cleats than is covered by flow passages.

13. The stent anchoring system of claim 1, wherein the tubular member has no holes extending through the thickness of the tubular member.

14. The stent anchoring system of claim 1, wherein some but not all of the plurality of clears are further symmetrical to an axially adjacent cleat.

15. A stent anchoring system for deployment in a lumen of a vessel, the system comprising:
   an expandable tubular member having a proximal end, a distal end, a longitudinal axis extending through the proximal and distal ends, an inner surface, an outer surface, a thickness between the inner surface and the outer surface, and a circumference in a plane perpendicular to the longitudinal axis; and
   a plurality of ribs extending outwardly from the outer surface of the expandable tubular member, each rib having an outer surface, a first lateral surface, and a second lateral surface, each rib spaced apart from a circumferentially adjacent rib, wherein each rib extends from the proximal end to the distal end of the tubular member and flow passages are positioned between circumferentially adjacent ribs, circumferentially adjacent ribs being symmetrical about the longitudinal axis of the tubular member; further wherein each rib has a wave-like pattern with peaks and troughs, and a peak of a first rib confronts a trough of a circumferentially adjacent rib.

16. The stent anchoring system of claim 15, further comprising a plurality of holes extending through the outer surface of the tubular member, the plurality of holes sized to allow transfer of fluid therethrough, each hole being positioned along a flow passage in a center of a region defined by a peak of one rib and a trough of a circumferentially adjacent rib.

17. The stent anchoring system of claim 16, wherein the plurality of holes are aligned in circumferential rows and in longitudinal rows.

18. The stent anchoring system of claim 15, wherein the ribs comprise a metal core covered in polymer.

19. The stent anchoring system of claim 2, wherein each cleat is symmetrical to each circumferentially adjacent surface protrusion about the longitudinal axis of the tubular member.

20. The stent anchoring system of claim 2, wherein the holes are aligned into longitudinal rows and into circumferential rows.

* * * * *